United States Patent [19]

Schulz et al.

[11] Patent Number: 5,514,101
[45] Date of Patent: May 7, 1996

[54] PISTAL GRIP IMPLANTATION DEVICE WITH PUSH BACK BAR

[75] Inventors: Dieter Schulz, Muehlheim; Karl Schreijaeg, Rottweil-Zepfenhan, both of Germany

[73] Assignee: Henke-Sass, Wolf GmbH, Tuttlingen, Germany

[21] Appl. No.: 253,954

[22] Filed: Jun. 3, 1994

[30] Foreign Application Priority Data

Mar. 25, 1994 [DE] Germany .............................. 9405144 U

[51] Int. Cl.$^6$ .................................................. A61M 31/00
[52] U.S. Cl. .................................. 604/61; 604/62; 604/60
[58] Field of Search .......................... 604/57, 59, 60–64, 604/134, 135; 221/76, 69, 71, 72, 74, 76, 78; 74/411

[56] References Cited

U.S. PATENT DOCUMENTS 4,762,515  8/1988  Grimm ........................................ 604/61

*Primary Examiner*—Corrine M. Maglione
*Assistant Examiner*—Michael L. Arness
*Attorney, Agent, or Firm*—McAulay Fisher Nissen Goldberg & Kiel

[57] ABSTRACT

A device for the implementation of pellets containing medication in animals comprises a housing in the shape of a pistol with a handle, a hollow needle for injecting the body of the animal arranged at the front side of the housing and a push rod adapted to being slid into the hollow needle and supported by the housing so as to be longitudinally displaceable. A shaft is also provided in the housing before the hollow needle for a magazine holding pellets which is displaceable therein. A longitudinally displaceable press-back device is arranged in the housing parallel to the push rod and hollow needle. A drawing mechanism is included in the housing for moving the push rod and press-back device. The mechanism is able to be set in motion by an operating lever fastened at the handle via a toothed segment coupled with the operating lever and via a toothed wheel engaging with the operating lever. The driving mechanism has a continuous toothed belt which is guided along a predetermined region of its length parallel to the push rod between two deflecting rollers and via a toothed belt pulley. The pulley is connected coaxially with the toothed wheel. The continuous toothed belt has a clamping part in the region extending parallel to the push rod. The clamping part is fastened to an end of the push rod located opposite the end of the push rod associated with the hollow needle.

6 Claims, 2 Drawing Sheets

PISTAL GRIP IMPLANTATION DEVICE WITH PUSH BACK BAR

BACKGROUND OF THE INVENTION a) Field of the Invention

The present invention is directed to a device for the implantation of pellets containing medication in animals, which device has a housing in the shape of a pistol with a handle, a hollow needle for injecting the body of the animal being arranged at the front side of the housing, and a push rod. The push rod can be slid into this hollow needle and is supported in the housing so as to be displaceable longitudinally. A shaft is provided in the housing prior to the needle for a magazine holding pellets which is displaceable therein. A longitudinally displaceable press-back device is arranged in the housing parallel to the push rod and hollow needle. The push rod and press-back device are moved by a driving mechanism which is similarly provided in the housing and which can be set in motion by an operating lever fastened at the handle via a toothed segment coupled with the operating lever and a toothed wheel engaging with the latter.

b) Description of the Related Art

In a device of this kind known from U.S. Pat. No. 4,447,223, the driving mechanism between the toothed segment and toothed wheel on one side and the push rod on the other side is formed by a gear unit which is connected between the latter and substantially includes an additional toothed wheel and a horizontal toothed rack of determined length which, in addition to moving the push rod through the pellet magazine and into the hollow needle, also drives the press-back device and advances the pellet magazine at the same time.

This driving mechanism works very directly, i.e. there is no play in the transmission of force between the toothed wheels and the toothed rack, and since the push rod is securely connected with the toothed rack, the latter can not move relatively to one another. Therefore, teeth can be broken off the toothed rack when the driving mechanism is overloaded, in particular when the device is soiled to some extent in this region.

It has already been suggested in DE-OS 41 06 196 to use a strip-shaped member as a driving mechanism for driving the push rod so that force may be transmitted from the operating lever to the push rod without the intermediary of a toothed rack and a toothed wheel engaging in the latter.

The strip-shaped member is a flat, resilient metal strip which is guided by its edges in two opposite U-shaped profiles or sections. One end of this strip is fastened to a wind-up drum which is driven by a toothed segment provided at the operating lever and by a toothed wheel which engages with the latter and is connected coaxially with the wind-up drum. The other end of the metal strip is fastened to the push rod. By moving the operating lever at the handle of the pistol-shaped implanting device, the wind-up drum rotates and winds up the metal strip so that the end fastened to the push rod is drawn forward and the push rod moves into the pellet magazine provided in the front part of the implanting device so that a pellet is pushed out of the latter and into the hollow needle and is pushed through the latter and implanted in the cavity formed in the body of the animal by the hollow needle.

The return movement of the push rod is not brought about by the metal strip, but rather by a spiral spring arranged on the push rod which is compressed when the push rod is drawn forward and presses the latter back into its initial position at the end of the implantation process. In so doing, the push rod draws the metal strip off the wind-up drum again so that the operating lever is also moved back into its initial position. This driving mechanism is relatively complicated and is therefore subject to frequent problems, particularly in that the metal strip guided in the U-shaped sections jams easily as the implanting device becomes dirty so as to impair the operating reliability of the device.

OBJECT AND SUMMARY OF THE INVENTION

The primary object of the present invention is to improve the known driving mechanisms in implantation devices in such a way that these implantation devices remain operational even when soiled and their driving mechanisms have good stability under load. In particular, the invention has the specific object of providing the driving mechanism with an elasticity inherent to the system which allows a more flexible transmission of force and prevents overloading of the push rod, wherein the pellet magazine is not driven via the push rod.

The stated objects are met in the device described above in that the driving mechanism substantially has an endless or continuous toothed belt which is guided along a determined region of its length parallel to the push rod between two deflecting rollers and via a toothed belt pulley which is connected coaxially with the toothed wheel, and in that the continuous toothed belt has a clamping part in its region extending parallel to the push rod, which clamping part is fastened to the end of the push rod located opposite the end of the push rod associated with the hollow needle.

This construction of the driving mechanism ensures the desired elasticity between the operating lever and toothed segment on the one hand and the push rod which loads the pellet through the hollow needle into the body of the animal on the other hand. Even if greater force must be exerted temporarily for overcoming an obstacle, e.g. dirt, a tooth will not be broken off from the toothed segment or from the toothed wheel engaging therewith, since the continuous toothed belt is pliant and resilient.

The operating lever advantageously has a second arm located opposite its axle for advancing the magazine holding the pellets. In contrast to known implantation devices, the magazine for pellets in the device according to the invention is advanced directly by the operating lever, that is, it is not first advanced via the driving mechanism and push rod. Accordingly, the loading of the push rod and the driving mechanism is reduced so as to increase the operating reliability of the device.

The continuous toothed belt is advantageously guided via an additional tension roller. This tension roller which can be spring-loaded, for example, ensures that the continuous toothed belt always contacts the toothed belt pulley in a positive engagement and accordingly guarantees a non-slip drive.

In a further development according to the invention, the press-back device is constructed as a rod. The injection end of the rod provided for support on the body of the animal is bent at a right angle to the hollow needle and guided in a U-shaped manner around the hollow needle. The end located in the housing is bent at a right angle to the push rod and angled over the latter in such a way that it can be driven by the clamping part. Since the injection end of the press-back device is guided around the hollow needle, the device is supported on the body of the animal during the press-back process so as to prevent tilting, particularly of the hollow needle in the body of the animal.

The region within which the push rod can move back and forth is advantageously defined by two stops arranged at a distance from one another in the housing. The length of this region can be changed by adjusting the stop situated toward the front side of the device corresponding to the length of the hollow needle to be used depending on the animal to be injected and/or the pellet to be implanted.

The end of the press-back device driven by the clamping part is advantageously arranged at a distance in front of the stop situated toward the front part of the housing when the device is not in operation, which distance approximately corresponds to the length of the hollow needle projecting out of the housing. The selected distance ensures that the pellet located in the hollow needle will be pushed out by means of the push rod at the same time that the hollow needle or entire device is withdrawn.

An embodiment example of the device for the implantation of pellets containing medication which explains the features of the invention is described in the following with reference to the drawings.

DESCRIPTION OF THE PREFERRED EMBODIMENTS

Figure 1:
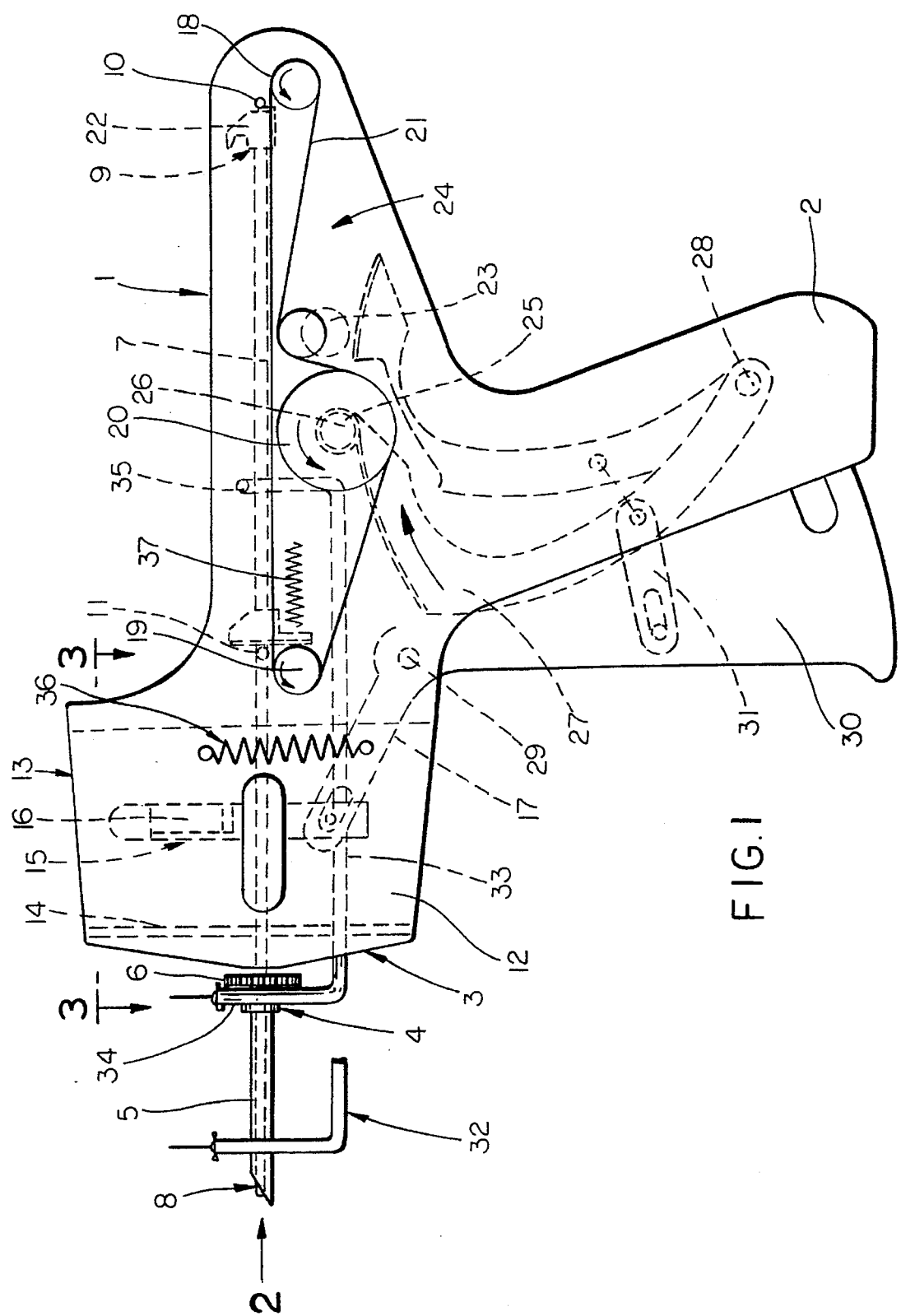
FIG. 1 shows a side view of the housing 1 of the device which is essentially shaped like a pistol with a handle 2.

A needle holder 4 is provided at the front side of the housing 1. The hollow needle 5 which pierces the body of the animal is secured at the needle holder 4 by means of a knurled screw 6.

A longitudinally displaceable push rod 7 which is guided into the hollow needle 5 by its end 8 on the injection side and can move back and forth between stops 10 and 11 provided in the housing 1 with its opposite end 9 is arranged in the housing 1 approximately in the region where, in pistols, the barrel for the ammunition is provided. A vertical shaft 13 is provided in the front part 12 of the housing 1 directly behind the needle holder 4 for the hollow needle 5. A magazine, not shown in the drawing, for receiving a supply of pellets can be inserted in the shaft 13. The shaft 13 has a guide slot 14 in which the magazine engages via a rail which is provided on the magazine and stabilizes the latter with respect to direction when the magazine is guided through the shaft 13. A mechanical driving device 15 constructed as a forward-feed spring 16 engaging in a catch provided at the magazine is formed in the wall region of the shaft 13. The forward-feed spring 16 can be moved downward by a lever arm 17 in such a way that the magazine, not shown, is adjusted downward stepwise and a pellet is introduced into the push rod region and accordingly in front of the hollow needle 5.

A continuous toothed belt 21 extends parallel to the push rod 7 in the region between the stops 10 and 11. The continuous toothed belt 21 is guided over two deflecting rollers 18 and 19 adjacent to the stops 10 and 11 and a toothed belt pulley 20 provided between the latter and can be moved back and forth by the toothed belt pulley 20 depending on the direction in which the latter rotates. The end 9 of the push rod 7 has a clamping part 22 which is fastened to the continuous toothed belt 21 and carried along by the latter, when driven, in the region between the stops 10 and 11. A tension roller 23, which can be adjusted by spring pressure, for example, is provided so that the continuous toothed belt 21 runs over the deflecting rollers 18 and 19 and over the toothed belt pulley 20 with good tension at all times.

The driving mechanism 24 described above is set in motion by a toothed wheel 25 which is fastened coaxially with the toothed belt pulley 20 on an axle 26. The toothed wheel 25 meshes with a toothed segment 27 which is swivelable around an axle 28 provided in the handle 2 and is actuated via an intermediate lever 31 by the operating lever 30 which is likewise provided at the handle 2 and swivelable around an axle 29.

The operating lever 30 at the axle 29 is connected with the lever arm 17 which advances the magazine (not shown) for the pellets via the driving device 15.

When the user of the device presses the operating lever 30 in the direction of the handle 2, the switching lever 17 is first moved downward. The magazine is accordingly pushed farther downward by one chamber or compartment so that a pellet is located in the movement path of the push rod 7 in front of the hollow needle 5. When the operating lever 30 is pressed in further, the toothed segment 27 is swiveled downward around the axle 28 via the intermediate lever 31 so that the toothed belt pulley 20 is rotated in this way via the toothed wheel 25 and the continuous toothed belt 21 is moved at the same time. The latter drives the clamping part 22 and accordingly pushes the push rod 7 in the direction of the hollow needle 5, wherein the end 8 of the push rod 7 on the injection side first strikes against the pellet, pushes it into the hollow needle 5 and finally pushes the pellet further into the cavity created by the hollow needle 5 when piercing the body of the animal.

In order for the pellet to be inserted into the body of the animal without being damaged, the hollow needle 5 must be pulled out of the body of the animal, that is, by withdrawing the entire device. At the same time, the push rod 7 pushes the pellet forward through the hollow needle 5 into the cavity formed in the body of the animal for as long as the hollow needle 5 or the device as a whole is being pulled out.

Figure 2:
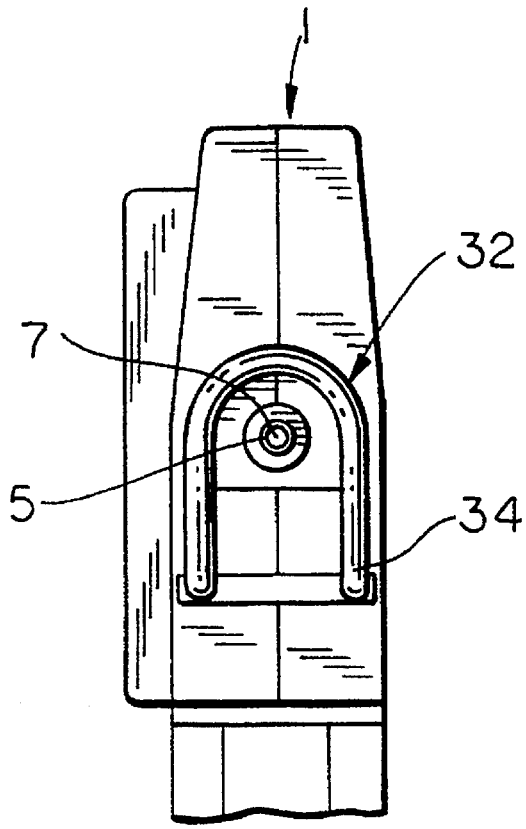
FIG. 2 is a partial front view taken from direction 2 of FIG. 1.
Figure 3:
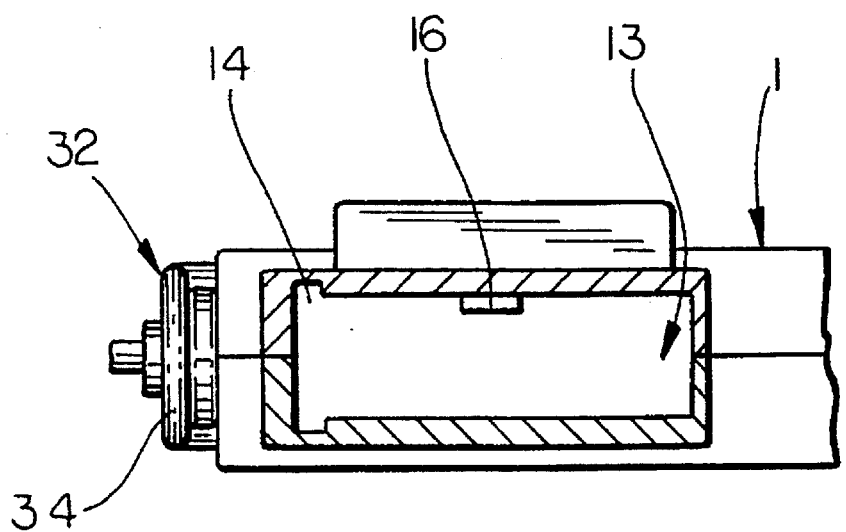
FIG. 3 is a partial sectional view taken along 3—3 of FIG. 3.

In order that this sequence of movements occurs synchronously, there is provided, in addition, a press-back device 32 essentially having the shape of a metal rod 33 which is supported by a slot 40 defined within the housing 1 so as to be displaceable longitudinally within the housing 1 parallel to the push rod 7. Referring to FIGS. 2 and 3, the front end 34 of the metal strip 33 on the injection side is bent at a right angle to the hollow needle 5 and is guided around the hollow needle 5 in a U-shaped manner in the form of a stirrup so that it can contact the body of the animal serving as a support.

The other end 35 of the press-back device 32 is also bent at a right angle to the push rod 7 and is angled over the latter so that it is driven by the correspondingly constructed clamping part 22 as soon as this clamping part 22 and the push rod 7, respectively, have been guided forward by the toothed belt 21 approximately two thirds of the distance away from the stop 10. After this point, a surface of the clamping part 32 engages the press-back device 32 to displace the press-back device 32 forward, that is, against the body of the animal, parallel to the push rod 7 and at the same speed as the latter. When this occurs, the device 1 is removed from the body of the animal and the hollow needle 5 is also pulled out of the body of the animal and in so doing the pellet is pushed out of the hollow needle 5 by the advancing push rod 7 and is inserted into the cavity formed in the body of the animal by the hollow needle 5.

At the end of the implantation process, the operating lever 30 returns to its initial position due to the force of the spring 36 provided at the lever arm 17 and the toothed segment 27 which returns simultaneously also moves back the toothed belt 21 and accordingly the push rod 7.

Driven by the additional spring 37 arranged at the press-back device 32, the latter also returns to its end position and, since it presses against the clamping part 22 with its bent end 35, reinforces the entire return movement of the push rod 7, toothed belt 21 and toothed segment 27 and finally also that of the operating lever 30. At the same time, the forward-feed spring 16 is pushed back into its initial position in order to move the magazine further downward by one compartment at the start of the next implanting process and to "reload" the device. When the push rod 7 is returned to its original position, no portion of the push rod 7 remains in the magazine section of the housing 1.

In contrast to the driving mechanism constructed by means of flat metal strips or toothed racks and the known lever-shaped gear units as in the prior art, it has been shown that the solution suggested and described herein which makes use of a continuous toothed belt guided via deflecting rollers and a toothed belt pulley has the required "internal" elasticity to ensure a reliable operation and also will not cease to function in spite of the inevitable soiling occurring in injection devices used in veterinary medicine. While the foregoing description and drawings represent the preferred embodiments of the present invention, it will be obvious to those skilled in the art that various changes and modifications may be made therein without departing from the true spirit and scope of the present invention.

What is claimed is:

1. A device for implanting pellets containing medication in an animal, said device comprising:

a housing in a shape of a pistol, said housing including a front surface, a handle attached thereto, and a slot defined therein:

a hollow needle for injecting a body of the animal, said hollow needle projecting from said front surface of said housing;

a push rod positioned within said housing, said push rod including a first end and a second end, said first end being displacable within said hollow needle;

a shaft provided in a port,on of said housing for receiving a magazine holding pellets;

a longitudinally displacable press-back device, said press-back device being supported for displacement with said push rod by said slot; and a driving means for displacing said push rod and press-back device, said driving means including: (i) an operating lever fastened to said handle by an axle: (ii) a toothed segment coupled to said operating lever: (iii) a toothed pulley attached to said housing, said toothed pulley containing a coaxially connected toothed wheel engaged with said toothed segment; (iv) deflecting rollers attached to said housing: (v) a continuous toothed belt which is guided around said toothed pulley and deflecting rollers; and, (vi) a clamping part which is attached to said continuous toothed belt to engage and displace said push rod and said press-back device;

wherein said operating lever includes an arm which is located opposite said axle for advancing said magazine holding pellets.

2. A device according to claim 1, further including a tension roller, wherein said continuous toothed belt is guided over said tension roller.

3. A device for implanting pellets containing medication in an animal, said device comprising:

a housing in a shape of a pistol, said housing including a front surface, a handle attached thereto, and a slot defined therein;

a hollow needle for injecting a body of the animal, said hollow needle projecting from said front surface of said housing;

a push rod positioned within said housing said push rod including a first end and a second end, said first end being displacable within said hollow needle;

a shaft provided in a portion of said housing for receiving a magazine holding pellets;

a longitudinally displacable press-back device, said press-back device being supported for displacement with said push rod by said slot; and a driving means for displacing said push rod and press-back device, said driving means including: (i) an operating lever fastened to said handle by an axle; (ii) a toothed segment coupled to said operating lever; (iii) a toothed pulley attached to said housing , said toothed pulley containing a coaxially connected toothed wheel engaged with said toothed segment; (iv) deflecting rollers attached to said housing; (v) a continuous toothed belt which is guided around said toothed pulley and deflecting rollers; and, (vi) a clamping part which is attached to said continuous toothed belt to engage and displace said push rod and said press-back device;

wherein said press-back device is a rod, including:

a first end provided for supporting the device on the body of the animal, said first end being formed in a U-shaped manner around said hollow needle, and a second end being supported within said housing by said slot, said second end being formed in a U-shaped manner around said push rod such that said second end is engaged and driven by said clamping part.

4. A device according to claim 2, further comprising first and second stops attached to said housing at a distance from one another to control movement of said clamping part, wherein said second end of said press-back device which is engaged by said clamping part is positioned at a distance from said first stop such that, when said device is not in operation, said distance approximately corresponds to a length of said hollow needle projecting from said front surface of said housing.

5. A device for implanting pellets containing medication in an animal, said device comprising:

a housing in a shape of a pistol, said housing including a front surface, a rear surface, a handle attached thereto, and a slot defined therein;

a hollow needle for injecting a body of the animal, said hollow needle projecting from said front surface of said housing;

a push rod positioned within said housing, said push rod including a first end and a second end, said first end being displacable within said hollow needle;

a shaft provided in a portion of said housing for receiving a magazine holding pellets;

a longitudinally displacable press-back device, said press-back device being supported for displacement with said push rod by said slot;

a driving means for displacing said push rod and press-back device, said driving means including: (i) an operating lever fastened to said handle by an axle; (ii) a toothed segment coupled to said operating lever; (iii) a toothed pulley attached to said housing, said toothed pulley containing a coaxially connected toothed wheel engaged with said toothed segment; (iv) deflecting rollers attached to said housing; (v) a continuous toothed belt which is guided around said toothed pulley and deflecting rollers; and, (vi) a champing part which is attached to said continuous toothed belt to engage and displace said push rod and said press-back device; and first and second stops which are attached to said housing at a distance from one another to control movement of said clamping part, wherein said first stop is positioned near said front surface of said housing and said second stop is positioned near said rear surface of said housing.

6. A device for implanting pellets containing medication in an animal, said device comprising:

a housing in a shape of a pistol, said housing including a front surface, a handle attached thereto, and a slot defined therein;

a hollow needle for injecting a body of the animal, said hollow needle projecting from a front surface of said housing;

a push rod positioned within said housing, said push rod including a first and second end, where said first end is displacable within said hollow needle and said second end contains a clamping part;

a shaft provided in a portion of said housing for receiving a magazine holding pellets;

a press-back device supported for displacement with said push rod by said slot, said press-back device further including (i) a first end for supporting the device on the body of the animal, said first end being formed in a U-shaped manner around said hollow needle, and (ii) a second end positioned within said housing, said second end being formed in a U-shaped manner around said push rod; and a driving means for displacing said push rod and press-back device, said driving means being connected to said handle and said clamping member, wherein, upon depressing said handle, said clamping member displaces said push rod and said press-back device.

* * * * *